(12) United States Patent
Roger et al.

(10) Patent No.: US 7,173,714 B2
(45) Date of Patent: Feb. 6, 2007

(54) APPARATUS FOR PARALLEL DETECTION OF THE BEHAVIOUR OF MECHANICAL MICRO-OSCILLATORS

(75) Inventors: Jean-Paul Roger, Quincy Sous Senart (FR); Albert Claude Boccara, Paris (FR); Christian Bergaud, Toulouse (FR); Marie-Claude Potier, Asnieres sur Seine (FR)

(73) Assignee: Centre National de la Recherche Scientifique (C.N.R.S.), Paris Cedex (FR)

( * ) Notice: Subject to any disclaimer, the term of this patent is extended or adjusted under 35 U.S.C. 154(b) by 408 days.

(21) Appl. No.: 10/415,984

(22) PCT Filed: Nov. 5, 2001

(86) PCT No.: PCT/FR01/03409

§ 371 (c)(1),
(2), (4) Date: Oct. 16, 2003

(87) PCT Pub. No.: WO02/37090

PCT Pub. Date: May 10, 2002

(65) Prior Publication Data

US 2004/0052687 A1   Mar. 18, 2004

(30) Foreign Application Priority Data

Nov. 6, 2000   (FR) .................................. 00 14215

(51) Int. Cl.
*G01B 9/02* (2006.01)

(52) U.S. Cl. ..................................... 356/492; 356/496
(58) Field of Classification Search ........ 356/491–493, 356/495, 501, 498, 511, 496, 512, 515
See application file for complete search history.

(56) References Cited

U.S. PATENT DOCUMENTS

| 5,445,008 | A | 8/1995 | Wachter et al. |
| 6,016,686 | A | 1/2000 | Thundat |
| 6,219,145 | B1 * | 4/2001 | Gutierrez et al. ........... 356/498 |
| 6,765,680 | B2 * | 7/2004 | Carr et al. .................. 356/510 |

* cited by examiner

*Primary Examiner*—Hwa (Andrew) Lee
(74) *Attorney, Agent, or Firm*—Young & Thompson

(57) ABSTRACT

The invention concerns an apparatus for parallel detection of the behaviour of mechanical micro-oscillators interacting with the sample (21). The amplitude and the phase of resonance of micro-oscillators (12) are measured with optical means. The invention is characterised in that a source (1) is active during a fraction 1/n of the period (n being an integer) and of variable phase p/n of the period (p being an integer). Interferences are produced between light beams generated by reflection of incident light beams (7) and (8) on the micro-oscillators (12). Periodically the micro-oscillators (12) are displaced by means. The value of the parameter p (p being an integer) is varied and N elementary measurements are integrated to obtain a measurement representing each of the values of p. The phase and amplitude of each micro-oscillator (12) are calculated on the basis of the representative data obtained for each value of p and this for a large number of accumulations. The invention is applicable in the field of nanotechnologies.

19 Claims, 2 Drawing Sheets

APPARATUS FOR PARALLEL DETECTION OF THE BEHAVIOUR OF MECHANICAL MICRO-OSCILLATORS

The present invention concerns an apparatus for parallel characterisation of the dynamic response of micro-levers or other mechanical micro-oscillators.

Nanotechnologies represent a field of research enjoying increasing interest in the scientific community since it appeared at the beginning of the 90s. Its name relates to its field of application which concerns objects in the order of a few nanometers to a few micrometers. To this day, the potentialities of such a field seem extremely vast, from microelectronic industry to biology and medicine.

The mechanical structures that can be manufactured today by techniques derived from micro-electronics (silicium, silica, nitride machining, etc.) play an important part in the realisation of sensors or actuators.

For example, in atomic force microscopy (AFM), the image of a surface is obtained by detecting the amplitude and the phase of the oscillations of a probe around the resonance. Said probe is composed of a lever mounted on a support which is subject to a resonant oscillation by a piezoelectric actuator. The resonance frequency of the lever is then disturbed by the interaction of the tip, fixed at its free end, with the surface to be imaged. Micromechanical oscillators, such as AFM levers may be used as probes for chemical, biological reactions, etc. In such a case, the oscillators are covered with reactive compounds, specific to a chemical or biological reaction that it is sought to be put in evidence. This reaction will be followed by a mass variation of the oscillator and therefore of its mechanical response (resonance for example).

The mechanical displacement of the lever may be detected in amplitude and in phase, for example by the deflexion of a laser beam focused on the free end of the lever. The reflected beam is then detected by a position detector which hence provides a measurement of the deformation of the lever. The data is acquired by scanning a frequency range situated around the resonance frequency of the lever.

However, such systems remain limited by the implementation of a very small number of levers. When measuring the mechanical resonance, the detection system enables to use only one lever. It is then a single detector. When detecting the static deformation, recent works carried out by Baller and al. [Ultramicroscopy; 82 (2000) 1] and Fritz and al. [Science, 288 (2000) 316] have shown the quasi simultaneous measurement of the deformations of a set of eight levers by a single detector.

These current systems do not enable simultaneous measurement of the resonance frequency of a very large number of levers.

Besides, a method and a device for multichannel analogic detection (patent FR-2 664 048) are known, whereof the performances have been demonstrated in the surface profilometry (sensitivity in the order of the picometer). With this method and this device, the signal to be detected is a modulated luminous signal. The reading frequency of the signals sent by the multichannel detector may be dissociated from the modulation frequency of the signal to be detected, thereby enabling to improve significantly the signal/noise ratio, independently of the modulation frequency.

The object of the present invention is therefore to suggest an apparatus which is simple in its design and its operating mode, implementing a multichannel detection device for parallel measurement of the amplitude and of the phase of the oscillations of a large number of micro-levers or other micromechanical oscillators, around the resonance.

To this end, the invention concerns an apparatus for parallel detection of the behaviour of mechanical micro-oscillators comprising:
  mechanical micro-oscillators mounted on a support, interacting with the sample,
  optical means for measuring the amplitude and the phase of the oscillations of the micro-oscillators.

According to the invention, said optical means comprise:
  a periodic luminous source, active during a fraction 1/n of the period (n integer) and of variable phase p/n of the period (p integer),
  means for producing incident luminous beams directed respectively to each of the micro-oscillator ends,
  means for splitting said incident luminous beams,
  interference means of the reflected and modulated luminous beams, generated by reflection of the incident luminous beams on the micro-oscillators, thereby producing an interference image,
  a multichannel detector comprising at least as many channels as there are micro-oscillators.

This apparatus comprises moreover:
  means for periodical displacement of the micro-oscillators as a whole,
  means enabling to vary the value of the parameter p (p integer) and to integrate N elementary measures to obtain a representative measurement for each value of p,
  a computer enables to record, in a buffer memory, the representative data obtained for each value of p and this, for a large number of accumulations. It then enables to calculate the phase and the amplitude of oscillations of each micro-oscillator.

Here, the expression "mechanical oscillator" will refer to a micro-lever such as a slim element of a length of several tens of micrometers, generally in the form of beam, connected to one of its ends, so-called first end, to the frame of the device by means of an elastic link.

Its other, or second end is in motion. The transversal movement of this second end is measured in order to characterise the sample.

Amongst usable mechanical oscillators, one should also mention the membranes for which the movement of a point forming generally the centre will be compared to another usually peripheral point.

By sample is meant chemical or biological species, regardless of the way they interact with the micro-oscillators. The only condition to be met by these samples is that their presence or their concentration affects the mechanical properties of the micro-oscillators.

In different particular embodiments each having its own advantages and compatible with numerous technically possible combinations:
  the means for periodical displacement of the micro-oscillators comprise piezoelectric ceramics, whereof the electric excitation frequency, synchronised with the luminous source, is f;
  the support is a silicon plate, mounted directly on the piezoelectric ceramics;
  the free end of the micro-oscillators is functionalised for selective and differentiated detection of the sample;
  the means for splitting the incident luminous beams comprise:
    a polarisation cube separator for linear polarisation of the incident luminous beam, a Wollaston prism for splitting the incident luminous beam into two orthogonally polarised beams;

the assembly composed of micro-oscillators, of the support and of the piezoelectric ceramics is placed on a bench, the assembly being at atmospheric pressure;

the means enabling to vary the value of the parameter p, to synchronise the detection, the luminous source and the piezoelectric ceramics comprise a sequencer;

the detection assembly contains a zoom and a digital CCD camera;

the detection assembly contains a microscope and an analogic camera.

The invention will be described more in detail with reference to the appended drawings wherein.

Figure 1:
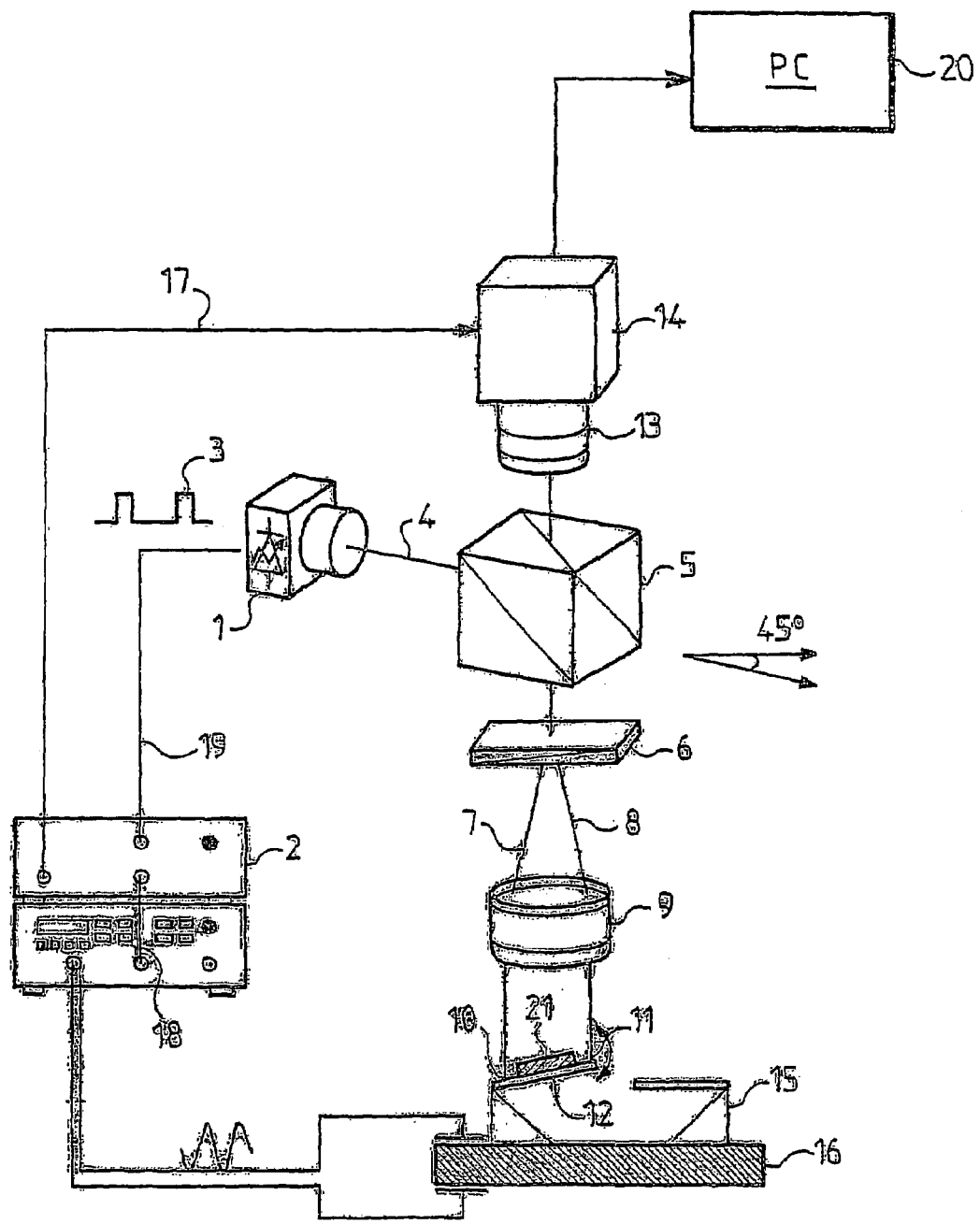
FIG. 1 is a schematic representation of the detection apparatus according to the invention.
Figure 2:
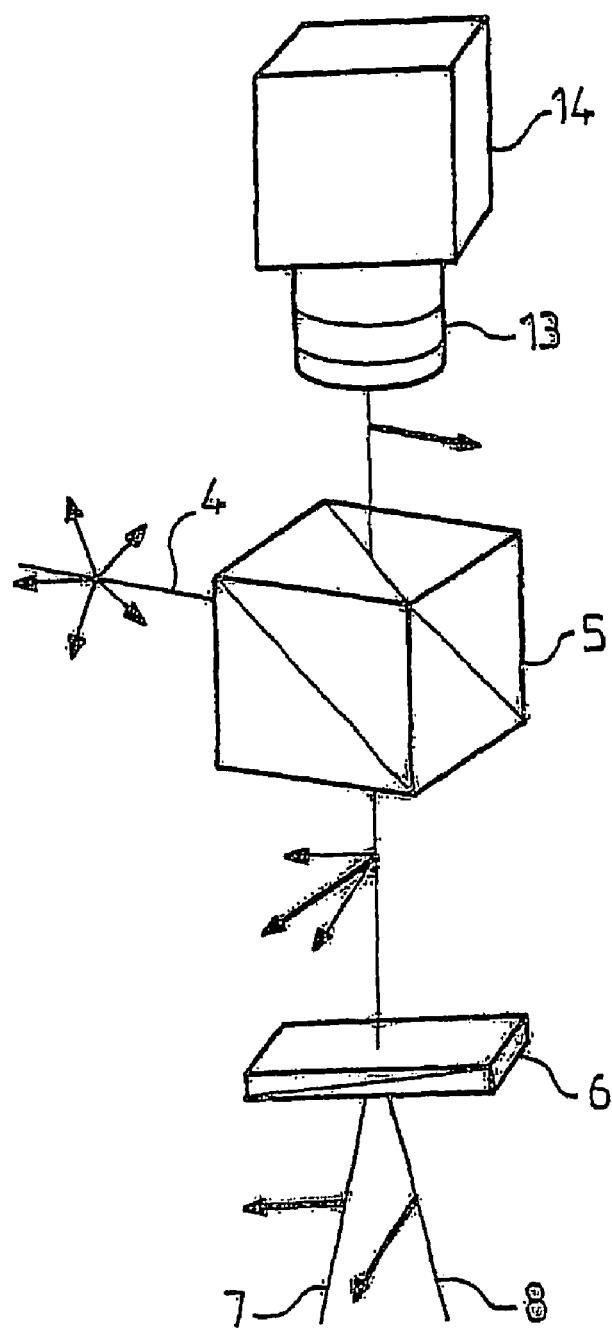
FIG. 2 represents the optical pathway of the polarisations.

A luminous source 1, for example a light-emitting diode, is controlled by a sequencer 2, so that it emits a periodical signal represented by a square function 3. This function takes the value 1 during a fraction 1/n of the period and a zero value outside. The optical axis of the beam 4 coming out of the luminous source 1 is oriented at 45° relative to the plan of FIG. 1.

Means for splitting and polarising the incident beam 4 are composed, for example of a polarisation cube separator 5 and of a Wollaston prism 6. The polarisation cube separator 5 produces a linearly polarised luminous beam in a direction at 45° relative to the optical axes of the Wollaston prism 6. The Wollaston prism 6 then separates the incident luminous beam 4 into two orthogonally polarised beams 7, 8. The polarised beams 7, 8 are then each focused by a lens 9 on one of the ends 10, 11 of a micro-oscillator 12.

The interference means are composed of the Wollaston prism 6, of the cube separator 5 and of a lens 13 which focuses the reflected beams, after interference, on the multichannel detector. The latter is composed of a CCD camera 14. The detection assembly is composed of the lens 13 and of the CCD camera 14.

Generally speaking, different types of interferometers enable the implementation of the invention. The micro-oscillators must be in a plane conjugated of the plane of the multichannel receiver, most often the pixel matrix of the camera.

The micro-oscillators 12 are beams of sizes 70×20 µm². The beams are made of a $SiO_2$ layer, 0.75 µm thick, covered by a gold layer 0.45 µm thick. The deposit of a gold layer enables to increase very significantly the reflection coefficient of the beams. The calculated resonance frequency of these beams is 120.19 KHz.

The micro-oscillators 12 are mounted on a support 15 which a silicon matrix. It is put in contact directly with piezoelectric ceramics 16 which ensures periodic displacement of the micro-oscillators 12. For maintaining good frequency response of the micro-oscillators 12, it is necessary to realise satisfactory coupling between the support 15 and the piezoelectric ceramics 16. Advantageously, such coupling is provided by a drop of paraffin oil, but the glue also gives good results.

The sequencer 2 controls the acquisition of the interference images 17 and synchronises the electric excitation signal 18 of the piezoelectric ceramics 16 and the triggering 19 of the luminous source 1.

A computer 20 enables to record, in a buffer memory, the representative data obtained for each value of phase p/n and this for a large number of accumulations. It then enables to calculate the oscillation phase and amplitude of each micro-oscillator 12.

In the device of FIG. 1, the luminous source 1 is active for a quarter of the period (n=4) and the phase value p/n is such that p varies from 0 to 3. Four interference images are then obtained by the CCD camera 14. Thanks to these four images, the amplitude and phase information of each micro-oscillator 12 may be extracted from the expressions described below.

Let us assume $I_{s,p}$ as the luminous intensity of the source 1, where p represents the number of the quarter of the activity period of the source, the expression of the intensity of the interference signal $I_p$ measured by the CCD camera 14 is written then as:

$$I_p = I_{s,p}[1 - \cos(\psi_w + \Delta \cos(\omega t + \phi))] \quad (1)$$

For small pulse oscillations ω of the micro-oscillator and for a position of the point 11 corresponding to the end of the micro-oscillator 12, the sum $\psi_w$ of the static phase-shifts due to the Wollaston prism 6 and to the static deformation of the micro-oscillator 12 is equal to π/2.

The expression (1) may then be simplified thus:

$$I_p \sim I_{s,p}[1 + \Delta \cos(\omega t + \phi)]$$

The expression $\Delta \cos(\omega t + \phi)$ represents the optical phase-shift due to the reflection of the beams 7 and 8 on the oscillating micro-oscillator 12. Δ is the amplitude of the oscillation of the micro-oscillators 12 expressed as an optical phase-shift and φ the electric phase-shift of the oscillation of the micro-oscillators 12 relative to the mechanical oscillation of the piezoelectric ceramics 16.

It is both these parameters φ and Δ that should be determined.

The signal measured by the camera 14 is the integral of $I_p$ over N periods. While taking into account the form of the luminous signal (square function), one obtains then:

$$S_p = (1/2\pi) I_o N 2\pi/\omega [\pi/2 + 2\Delta \sin(\pi/4) \cos(p\pi/2 + \phi - \psi_s)]$$

where $\psi_s$ is the electric phase-shift between the luminous source 1 and the excitation electric reference of the piezoelectric ceramics 16. It also includes the phase-shift between the electric excitation 18 of the ceramics 16 and its mechanical response. $I_o$ represents the luminous intensity cut by the power supply of the source 1 (light-emitting diode).

The following can be deduced:

$$S_0 + S_1 + S_2 + S_3 = I_0 N \frac{2\pi}{\omega}$$

$$\tan(\phi - \psi_s) = (S_3 - S_1)/(S_0 - S_2)$$

$$\Delta = \pi/\sqrt{2} \times 1/(S_0 + S_1 + S_2 + S_3) \times \sqrt{[(S_3 - S_1)^2 + (S_0 - S_2)^2]}$$

The acquisition of the four images Sp (p=0 à 3) thus enables to determine completely the amplitude and the phase of the oscillations of the micro-oscillators 12.

The operation of the device of the invention is as follows:

The luminous source 1 generates, after going through a polarisation cube separator 5 and a Wollaston prism 6, two incident beams 7 and 8 forming, together, a small angle (in the order of the milliradian) and of orthogonal polarisations. The incident polarised beams 7 and 8 are then focused by the lens 9 on the ends 10 and 11 of a micro-oscillator 12. These polarised beams are then modulated by their reflection on the micro-oscillator 12. The Wollaston prism 6 is placed in the focal plane of the lens 9. The reflected beams, polarised and modulated, go then through, after reflection on the micro-oscillators, whereas the Wollaston prism 6 follows the reversed optical pathway. After going through, in return, the cube separator 5, the modulated polarised beams are focused by a lens 13 on the multichannel detector. The pixels of the CCD camera 14 thus detect the signal after interference. The signal received by a pixel of the CCD camera 14 depends then on the optical path difference between the beams 7 and 8, and hence on the amplitude difference between the points 10 and 11 of the micro-oscillator 12.

The description of the operation is based on considering only the polarised beams 7 and 8 but the diameter of the irradiated zone, at the surface, by the luminous source 1 relates to active zone of the luminous source 1, of the collimation lens of the beam 4 and of the focalisation lens 9. For the focal lens 9 and the luminous source 1 considered on FIG. 1, the diameter of the irradiated zone is 2.35 mm. The set of signals received on the different pixels of the CCD camera 14 enables therefore to determine the oscillation amplitude and phase of a large set of micro-oscillators 12. The pixels of the CCD camera 14 are read after storing a number N of elementary measurements, for each value of phase p/n. The refreshing frequency of the pixel matrix is therefore f/N. It is then possible to follow modulation frequencies of the micro-oscillators 12 in the order of several hundreds of KHz.

The selection of the focal length of the lens 9 must represent a compromise between satisfactory optical resolution and sufficient distance d separating the ends 10 and 11. The distance d is proportional to the focal length of the lens 9. By selecting high magnification and hence better optical resolution, the distance d separating the points 10 and 11 is then diminished to the extent of not being able any longer to detect the real amplitude difference of the ends of the micro-oscillator 12. For the lens 9 of focal length 50 mm and a lens 13 of focal length 300 mm considered on FIG. 1, the offset between 10 and 11 is 70 μm, the optical resolution is 2.7 μm.

This sample characterisation apparatus 21 may advantageously be used within the framework of the detection of chemical or biological species. The functionalisation of the free end 11 of the micro-oscillators 12 leads, indeed, to selective and differentiated adsorption of species. The resulting variation in mass offsets the resonance frequency of the active micro-oscillators 12 relative to that of an inert micro-oscillator 12 for the specie considered. It is thus possible to deduce the mass of the adsorbate therefrom.

With the possibility of simultaneous detection, thanks to multiplexed imaging technique, of the mechanical responses of a large number of micro-oscillators 12, this apparatus enables advantageously the acquisition of multiple data. It becomes, then, possible to obtain by an apparatus simple of use and of implementation, differentiated and multiple data on a sample 21 to be analysed.

The invention claimed is:

1. An apparatus for parallel detection of the behaviour of mechanical micro-oscillators, comprising:
   a support (15);
   a multichannel detector (14)
   a plural number of mechanical micro-oscillators (12) mounted on the support (15) and positioned for interacting with a sample (21), each micro-oscillator having a micro-oscillator end (10, 11) and an output; and
   an optical means for measuring an amplitude and a phase of oscillations produced by the micro-oscillators (12), said optical means comprising i) a periodic luminous source (1) for generating an incident luminous beam (4), the luminous source active during a fraction 1/n of a period (n integer) and with a variable phase (p/n) of the period (p integer),
   ii) operatively connected to an output of the luminous source, to receive the incident luminous beam (4) from the luminous source, a means for splitting and polarizing the incident luminous beam comprising
   a) a means for producing, from the incident luminous beam (4), a reflected and modulated luminous beam, and
   b) a means for splitting said reflected and modulated luminous beams into separate polarized beams (7, 8) directed to each of the micro-oscillator ends (10, 11), and
   iii) an interference means operatively connected to a) the means for producing reflected and modulated luminous beams and b) the outputs of the micro-oscillators (12), the interference means producing an interference image of the reflected and modulated luminous beams based on the outputs of the micro-oscillators (12), the interference image being directed to the multichannel detector; and
   the multichannel detector (14) comprising
   i) plural channels equal in number to at least the plural number of micro-oscillators,
   ii) a means for periodical displacement of the micro-oscillators (12) as a group (21),
   iii) a means to vary the value of the period of the luminous source and to integrate plural elementary measures to obtain a representative measurement for each value of the period, and
   iv) a computer (20) enabled to record, in a buffer memory, representative data obtained for each value of the period for a number of accumulations and then enabled to calculate the phase and the amplitude of each micro-oscillator (12).

2. An apparatus according to claim 1, wherein,
   the means for periodical displacement of the micro-oscillators comprises piezoelectric ceramics (16) with an electrical excitation frequency (18) synchronized with the luminous source (1).

3. An apparatus according to claim 2, wherein,
   the support (15) is a silicon plate, mounted directly on the piezoelectric ceramics (16).

4. An apparatus according to claim 1, wherein, a free end (11) of the micro-oscillators (12) is functionalized for selective and differentiated detection of the sample (21).

5. An apparatus according to claim 1, wherein,
   the means for producing reflected and modulated luminous beams comprises a polarization cube separator (5) for linear polarization of the incident luminous beam, and
   the means for splitting said reflected and modulated luminous beam into separate polarized beams (7, 8) directed to each of the micro-oscillator ends (10, 11) comprises a Wollaston prism (6) for splitting the reflected and modulated luminous beam into two orthogonally polarized beams (7, 8).

6. An apparatus according to claim 2, wherein,
   an assembly composed of the micro-oscillators (12), of the support (15) and of the piezoelectric ceramics (16) is placed on a bench, the assembly being at atmospheric pressure.

7. An apparatus according to claim 1, wherein,
   a means to vary the value of the period of the luminous source comprises a sequencer (2) operatively connected to synchronize detection (17) of the interference image, operation of the luminous source (1) and operation of the piezoelectric ceramics (16)).

8. An apparatus according to claim 1, wherein, the multichannel detector comprises a zoom (13) and a digital CCD camera (14).

9. An apparatus according to claim 1, wherein, the multichannel detector comprises a microscope and an analogic camera.

10. An apparatus according to claim 3, wherein, an assembly composed of the micro-oscillators (12), of the support (15) and of the piezoelectric ceramics (16) is placed on a bench, the assembly being at atmospheric pressure.

11. An apparatus for parallel detection of the behaviour of mechanical micro-oscillators, comprising:
plural micro-oscillators (12) with outputs;
a multi-channel detector;
a luminous source (1);
a sequencer (2) controlling the luminous source so that the luminous source emits a periodical incident beam (4) represented by a function (3) taking a first value during a fraction (1/n) of a period and another value outside the fraction of the period;
connected to receive the incident beam, a means for splitting and polarizing the incident beam comprised of a polarization separator (5) and of a prism (6), the polarization separator producing a linearly polarized luminous beam directed toward the prism, the prism separating the polarized luminous beam into orthogonally polarized beams (7, 8) directed respectively toward each of the micro-oscillators; and
an interference means operatively connected to the separator and to the outputs of the micro-oscillators and comprised of a lens (13), with an interference based on the output of the micro-oscillators, the lens focusing reflected beams of the separator on the multichannel detector,
the multichannel detector (14) comprising
i) plural channels equal in number to at least the plural micro-oscillators,
ii) a means for periodical displacement of the micro-oscillators (12) as a group (21),
iii) a means to vary the value of the period of the luminous source and to integrate plural elementary measures to obtain a representative measurement for each value of the period, and
iv) a computer (20) enabled to record representative data obtained for each value of the period for a number of accumulations and then enabled to calculate the phase and the amplitude of each micro-oscillator (12).

12. The apparatus of claim 11, wherein, the detector further comprises a CCD camera (14).

13. The apparatus of claim 11, wherein, the micro-oscillators have a calculated resonance frequency of 120.19 KHz.

14. The apparatus of claim 11, wherein, the micro-oscillators are comprised of piezoelectric ceramics (16) to move the micro-oscillators as a group.

15. The apparatus of claim 14, wherein, the sequencer controls acquisition of the interference images, synchronization of the piezoelectric ceramics and triggering of the luminous source.

16. The apparatus of claim 15, wherein, the sequencer controls the luminous source to be active for a quarter of the period with a varying phase value.

17. An apparatus for parallel detection of the behaviour of mechanical micro-oscillators, comprising:
plural mechanical micro-oscillators (12) with outputs;
a multi-channel detector;
a luminous source (1);
a sequencer (2) controlling the luminous source so that the luminous source emits a periodical incident beam (4) active during a fraction of a varying period;
a polarization separator (5);
a prism (6),
the polarization separator (5) connected to receive the incident beam from the luminous source and reflect the beam producing a linearly polarized luminous beam directed toward the prism,
the prism separating the polarized luminous beam into orthogonally polarized beams (7, 8) directed respectively toward each of the micro-oscillators; and
an interference means operatively connected to the separator and to the outputs of the micro-oscillators and comprised of a lens (13), with an interference based on the output of the micro-oscillators, the lens focusing reflected beams of the separator on the multichannel detector to produce interference images,
the multichannel detector (14) comprising
i) plural channels equal in number to at least the plural micro-oscillators,
ii) a means for periodical displacement of the micro-oscillators (12) as a group (21),
iii) a means to vary the value of the period of the luminous source and to integrate plural elementary measures to obtain a representative measurement for each value of the period, and
iv) a computer (20) enabled to record representative data obtained for each value of the period for a number of accumulations and then enabled to calculate the phase and the amplitude of each micro-oscillator (12).

18. The apparatus of claim 17, wherein, the sequencer controls acquisition of the interference images, synchronization of movement of the micro-oscillators, and triggering of the luminous source.

19. The apparatus of claim 18, wherein, the sequencer controls the luminous source to be active for a quarter of the period with a varying phase value.

* * * * *